(12) United States Patent
Sachs et al.

(10) Patent No.: US 8,624,045 B2
(45) Date of Patent: Jan. 7, 2014

(54) PROCESS FOR OLEFIN OXIDE PRODUCTION

(75) Inventors: Howard Sachs, Bronx, NY (US); Andrzej Rokicki, Mountain Lakes, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 262 days.

(21) Appl. No.: 12/970,404

(22) Filed: Dec. 16, 2010

(65) Prior Publication Data

US 2011/0152551 A1    Jun. 23, 2011

Related U.S. Application Data

(60) Provisional application No. 61/287,441, filed on Dec. 17, 2009.

(51) Int. Cl.
  *C07D 301/03*    (2006.01)

(52) U.S. Cl.
  USPC ........................................ 549/536

(58) Field of Classification Search
  USPC ........................................ 549/536
  See application file for complete search history.

(56) References Cited

U.S. PATENT DOCUMENTS

| | | | |
|---|---|---|---|
| 2,279,469 A | 4/1942 | Law et al. | |
| 3,563,914 A | 2/1971 | Wattimena | |
| 3,702,259 A | 11/1972 | Nielsen | |
| 4,761,394 A | 8/1988 | Lauritzen | |
| 4,766,105 A | 8/1988 | Lauritzen | |
| 4,874,879 A | 10/1989 | Lauritzen et al. | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,155,242 A | 10/1992 | Shankar et al. | |
| 5,187,140 A | 2/1993 | Thorsteinson et al. | |
| 5,407,888 A | 4/1995 | Herzog et al. | |
| 2004/0014999 A1 | 1/2004 | Chipman et al. | |
| 2007/0037991 A1 | 2/2007 | Rizkalla | |
| 2009/0082584 A1 | 3/2009 | Rizkalla et al. | |

FOREIGN PATENT DOCUMENTS

| EP | 0352850 B1 | 1/1994 |
|---|---|---|
| GB | 1055147 | 1/1967 |
| JP | 2002248351 | * 9/2002 |

OTHER PUBLICATIONS

Wasilewski Jerzy, Effect of some halogen inhibitors on the ethylene-to -ethylene oxide oxidation process using a stationary silver catalyst, Zeszyty Naukowe—Instytut Ciezkiej Syntezy Organiczej, 1970, 2(7), 128p.*

Lambert, R. M., et al., "Halogen-induced selectivity in heterogeneous epoxidation is an electronic effect-fluorine, chlorine, bromine and iodine in the Ag-catalysed see active oxidation of ethene", Chemical Communications, First published as an advanced article on the web: Apr. 16, 2003, No. 10, pp. 1184-1185.

Montrasi, G. L., et al., "Oxidation of Ethylene to Ethylene Oxide: Role of Organic Chlorides", Oxidation Communications 3, 1983, No. 3-4, pp. 259-267.

International Search Report dated Sep. 23, 2011 received in a corresponding foreign application.

* cited by examiner

*Primary Examiner* — Taylor Victor Oh
(74) *Attorney, Agent, or Firm* — Scully, Scott, Murphy & Presser, P.C.

(57) ABSTRACT

A process for the epoxidation of an olefin is disclosed which includes: reacting a feed gas composition containing an olefin, oxygen, and a moderator selected from the group consisting of diatomic chlorine and perhalogenated hydrocarbons, in the presence of an epoxidation catalyst.

13 Claims, No Drawings

PROCESS FOR OLEFIN OXIDE PRODUCTION

RELATED APPLICATIONS

This application claims benefit of U.S. Provisional Patent Application Ser. No. 61/287,441, filed Dec. 17, 2009, the entire content of which is incorporated herein by reference.

BACKGROUND OF THE INVENTION

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Theodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2000 was about 15 billion tons. (About two thirds of the ethylene oxide produced is further processed into ethylene glycol, while about ten percent of manufactured ethylene oxide is used directly in applications such as vapor sterilization.)

The growth in the production of ethylene oxide has been accompanied by continued intensive research on ethylene oxide catalysis and processing, which remains a subject of fascination for researchers in both industry and academia. Silver catalysts remain today the primary catalytic material for ethylene oxide production, but a number of advances have been made, most notably the efficacy of silver-based catalysts have been made by the addition of small amounts of "promoting" elements such as rhenium and cesium. Nonetheless, despite the extensive research there is still uncertainty over aspects of ethylene oxide catalysis, most notably the role of the silver catalyst and the precise reaction mechanism.

Chlorine has long been used in the feed mixture for the gas phase production of ethylene oxide (see e.g., Law et al., U.S. Pat. No. 2,279,469, issued Apr. 14, 1942; U.K. Pat. No. 1,055,147 issued Jan. 18, 1967, and Lauritzen, EPO Pat. No. 0 352 850 B1, issued Jan. 19, 1994) and has been variously known as an "inhibitor", "moderator", "anti-catalyst", and "promoter".

While chlorine's role was not fully understood in these prior publications, recent research indicates that chlorine regulates the reaction by withdrawing valence charge from surface-adsorbed oxygen atoms; chlorine is particularly suitable for this because chlorine's affinity for valence electrons is comparable to that of monoatomic oxygen. (See, Richard M. Lambert, Rachael L. Cropley, Alifiya Husain and Mintcho S. Tikhov, Chem. Comm., 2003, 1184-1185). Lower valence charge density of monoatomic adsorbed oxygen makes it a better electrophile, and thus energetically favors "electrophilic attack" on adsorbed ethylene and thus the partial oxidation of ethylene to ethylene oxide. Thus, chlorine plays a key role in maintaining the catalyst's selectivity—the efficiency of the partial oxidation of ethylene to ethylene oxide.

While prior publications have disclosed the use of chlorine under specific conditions, given the importance of chlorine on determining selectivity, and the results of recent studies into chlorine's role in epoxidation, the use of chlorine and the full range of chlorine-containing molecules have not been sufficiently explored. There is thus a continuing need in the art for a suitable chlorine composition for use in olefin epoxidation.

BRIEF SUMMARY OF THE INVENTION

The present invention relates to a process for the epoxidation of an olefin, including: reacting a feed gas composition containing an olefin, oxygen, and a moderator selected from the group consisting of diatomic chlorine and perhalogenated hydrocarbons, in the presence of an epoxidation catalyst.

The present invention further relates to a kit for the epoxidation of an olefin including: (a) an epoxidation catalyst; (b) a feed gas composition containing an olefin, oxygen, and a hydrogen-free chlorine source selected from the group consisting of diatomic chlorine and perhalogenated hydrocarbons; and (c) a reactor for reacting the components of the gas feed composition in the presence of an epoxidation catalyst.

DETAILED DESCRIPTION OF THE INVENTION

The present invention is directed to the gas phase epoxidation of an olefin to form an olefin oxide by contacting a silver-based catalyst in a reactor with a feed that contains at least oxygen, an olefin, and a chlorine-containing moderator. It has been surprisingly discovered in the present invention that hydrogen-free chlorine sources such as perhalogenated hydrocarbons and diatomic chlorine are particularly effective as moderators in gas phase epoxidation. Although not wishing to be bound by theory, the theoretical explanation for the effectiveness of such chlorine-containing species is discussed above. Perhalogenated hydrocarbons refer to organic molecules in which all of the hydrogen atoms in a hydrocarbon have been substituted with halogen atoms; suitable examples are trichlorofluormethane and perchloroethylene. The use of these hydrogen-free chlorine sources are particularly aimed at improving basic and novel performance characteristics of the catalyst including, but not limited to, catalyst selectivity, stability, and activity.

The aforementioned moderators may be used in combination with other moderators, non-limiting examples of which include organic halides such as $C_1$ to $C_8$ halohydrocarbons; especially preferred is methyl chloride, ethyl chloride, ethylene dichloride, vinyl chloride or mixtures thereof.

Preferably a single chlorine-containing moderator is used from the outset; although less preferred, two different moderator species may be fed into the reactor either simultaneously or sequentially. For example, during start-up (or "conditioning") of a fresh silver-based catalyst batch, ethyl chloride may be used, and with the ethyl chloride feed continuing, diatomic chlorine may be fed at gradually increasing concentration levels (with concomitant decreases in the ethyl chloride concentration) until the moderator feed is entirely diatomic chlorine.

The concentration level of the moderator must be controlled so as to balance a number of competing performance characteristics; for example, moderator concentration levels that result in improved activity may simultaneously lower selectivity. Another factor in the concentration level of the moderator is the type of silver-based catalyst in the reactor, specifically whether the catalyst contains rhenium. As rhenium-containing catalyst ages the moderator concentration is carefully monitored so as to continually increase, within very small increments, the moderator concentration because optimal selectivity values are obtained only within a narrow moderator concentration range. Non-rhenium containing catalysts are less sensitive to the moderator levels, and the moderator concentration needs to be adjusted upwards only a few times during the service life of a catalyst charge; nonetheless because the moderator does partly inhibit the epoxidation reaction, higher levels of moderator have a deleterious effect on the activity of a non-rhenium containing catalyst and so moderator levels need to be carefully controlled.

Accordingly, for the moderators of the present invention, when used with a high-selectivity catalyst, the preferred range for perhalogenated hydrocarbons is from about 0.1 ppm to about 20 ppm, preferably about 0.4 ppm to about 10 ppm (by volume); for molecular diatomic chlorine gas the preferred range is about 1 ppm to about 75 ppm, preferably about 3 ppm to about 50 ppm (by volume).

As mentioned above the chlorine moderator is utilized as part of a gas phase epoxidation of an olefin to form an olefin oxide in the presence of a silver-based catalyst. The silver-based catalyst and epoxidation process will now be described in greater detail.

Silver-Based Epoxidation Catalyst

The silver-based epoxidation catalyst includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed may be selected from a large number of solid, refractory supports that may be porous and may provide the preferred pore structure. Alumina is well known to be useful as a catalyst support for the epoxidation of an olefin and is the preferred support. The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combinations thereof. The support may comprise at least about 95 wt. % alpha-alumina; preferably, at least about 98 wt. % alpha-alumina. The remaining components may include inorganic oxides other than alpha-alumina, such as silica, alkali metal oxides (e.g., sodium oxide) and trace amounts of other metal-containing or non-metal-containing additives or impurities.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. (Equivalent diameter is the diameter of a sphere having the same external surface (i.e., neglecting surface within the pores of the particle) to volume ratio as the support particles being employed.)

Suitable supports are available from Saint-Gobain Norpro Co., Sud Chemie AG, Noritake Co., CeramTec AG, and Industrie Bitossi S.p.A. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Additional optional components that may be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

Epoxidation Process

The epoxidation process may be carried out by continuously contacting an oxygen-containing gas with an olefin, preferably ethylene, in the presence of the previously-described catalyst. Oxygen may be supplied to the reaction in substantially pure molecular form or in a mixture such as air. By way of example, reactant feed mixtures may contain from about 0.5% to about 45% ethylene and from about 3% to about 15% oxygen, with the balance comprising comparatively inert materials including such substances as carbon dioxide, water, inert gases, other hydrocarbons, and the reaction moderators described above. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum. In one embodiment, the concentration of carbon dioxide in the feed gas is less than about 2%.

A usual method for the ethylene epoxidation process comprises the vapor-phase oxidation of ethylene with molecular oxygen, in the presence of the previously-described catalyst, in a fixed-bed tubular reactor. Conventional, commercial fixed-bed ethylene-oxide reactors are typically in the form of a plurality of parallel elongated tubes (in a suitable shell)

approximately 0.7 to 2.7 inches O.D. and 0.5 to 2.5 inches I.D. and 15-53 feet long filled with catalyst. Such reactors include a reactor outlet which allows the olefin oxide, un-used reactant, and byproducts to exit the reactor chamber.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 to about 20 seconds.

The resulting ethylene oxide, which exits the reactor through the reactor outlet, is separated and recovered from the reaction products using conventional methods. For this invention, the ethylene epoxidation process may include a gas recycle wherein substantially all of the reactor effluent is readmitted to a reactor inlet after substantially or partially removing the ethylene oxide product and the byproducts including carbon dioxide.

The previously-described catalysts have been shown to be particularly selective for oxidation of ethylene with molecular oxygen to ethylene oxide especially at high ethylene and oxygen conversion rates. The conditions for carrying out such an oxidation reaction in the presence of the catalysts described above broadly comprise those described in the prior art. This applies to suitable temperatures, pressures, residence times, diluent materials, moderating agents, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production rate (work rate) of 7-20 lbs. EO/cu.ft. catalyst/hr. The feed composition at the reactor inlet may typically comprises (by volume %) 5-40% ethylene, 3-12% $O_2$; 0.3% to 20%, preferably 0.3 to 5%, more preferably 0.3 to 1% of $CO_2$; 0-3% ethane, an amount of one or more chloride moderators as described above; and the balance of the feed being comprised of argon, methane, nitrogen or mixtures thereof.

EXAMPLES

The invention will now be described in more detail with respect to the following non-limiting examples.

Rhenium-containing catalyst pellets were crushed, ground and screened to provide a sample of 14-18 mesh particles. 6.5 grams of the material were then charged to a ¼" outer diameter heated microreactor. The reactor was heated to 200° C. and a feed gas having a composition of 0.08 ppm (by volume) perchloroethylene, 8% $C_2H_4$, 4% $O_2$, 4% $CO_2$, balance $N_2$, was introduced. The temperature was ramped to 245° C. over 50 hours, and then held at the temperature for an additional 65 hours. The feed gas was set to 25% $C_2H_4$, 7% $O_2$, and 2% $CO_2$ (balance nitrogen), and the temperature continually adjusted to maintain a ΔEO of 2.2%.

The perchloroethylene concentration was varied to determine its effect on selectivity. Excellent performance, with selectivity values of between 90% and 92.5%, was obtained by using perchloroethylene at concentration levels of between 0.8 ppm and 1.1 ppm (by volume). Such selectivity performance was long-lasting, being maintained at run times of 640 hours.

At 640 hours, the supply of perchloroethylene to the reactor was stopped and replaced by the conventional chlorine-source moderator ethyl chloride for 150 hours. Diatomic chlorine was then added to the feed gas for a period and the concentration varied between 1.5 ppm and 5 ppm (by volume). Excellent selectivity performance, with selectivity values of over 91%, was obtained by using diatomic chlorine at concentration levels of around 5 ppm (by volume).

Such selectivity performance obtained by the use of hydrogen-free chlorine source moderators such as perhalogenated hydrocarbons (i.e., perchloroethylene) and diatomic chlorine would not have been expected to a person of ordinary skill in the art.

It will be appreciated by those skilled in the art that changes could be made to the embodiments described above without departing from the broad inventive concept thereof. It is understood therefore that this invention is not limited to the particular embodiments disclosed, but it is intended to cover modifications within the spirit and scope of the present invention as defined by the appended claims.

We claim:

1. A process for the epoxidation of an olefin, comprising:
   reacting a feed gas composition containing an olefin, oxygen, and a first moderator selected from a $C_1$-$C_8$ halohydrocarbon in the presence of an epoxidation catalyst, wherein said $C_1$-$C_8$ halohydrocarbon is present in said feed gas composition at a first concentration; and
   gradually adding to said feed composition a second moderator selected from the group consisting of diatomic chlorine and perhalogenated hydrocarbons, while simultaneously decreasing the first concentration of said first moderator in the feed gas composition until no first moderator is present in the feed gas composition.

2. The process according to claim 1, wherein the second moderator is diatomic chlorine.

3. The process according to claim 1, wherein the second moderator is a perhalogenated hydrocarbon selected from the group consisting of trichlorofluoromethane and perchloroethylene.

4. The process according to claim 1, wherein the second moderator is diatomic chlorine present in a concentration of from about 1 ppm to about 75 ppm (by volume).

5. The process according to claim 1, wherein the second moderator is a perhalogenated hydrocarbon present in a concentration of from about 0.1 ppm to about 20 ppm (by volume).

6. The process according to claim 1, wherein the epoxidation catalyst contains a support, a catalytically effective amount of silver or a silver-containing compound, a promoting amount of rhenium or a rhenium-containing compound, and a promoting amount of one or more alkali metals or alkali-metal-containing compounds.

7. The process according to claim 6, wherein the second moderator is diatomic chlorine present in a concentration of from about 1 ppm to about 75 ppm (by volume).

8. The process according to claim 6, wherein the second moderator is a perhalogenated hydrocarbon present in a concentration of from about 0.1 ppm to about 20 ppm (by volume).

9. The process according to claim 1, wherein the epoxidation catalyst contains a support, a catalytically effective amount of silver or a silver-containing compound, a promoting amount of rhenium or a rhenium-containing compound, and a promoting amount of one or more alkali metals or alkali-metal-containing compounds and wherein the feed gas composition contains less than about 2% carbon dioxide.

10. The process according to claim 1, wherein the olefin is ethylene.

11. The process according to claim 6, wherein the epoxidation catalyst further includes promoting amounts of a Group IIA alkaline earth metal component.

12. A process for the epoxidation of an olefin, comprising:
reacting a feed gas composition containing an olefin, oxygen, and, a moderator composition consisting essentially of trichlorofluoromethane, in the presence of an epoxidation catalyst.

13. The process according to claim 12, wherein trichlorofluoromethane is present in a concentration of from about 0.1 ppm to about 20 ppm (by volume).

* * * * *